(12) United States Patent
Lee et al.

(10) Patent No.: US 10,538,853 B2
(45) Date of Patent: *Jan. 21, 2020

(54) METHOD AND APPARATUS FOR INCREASING A LIFESPAN OF NANOPORE-BASED DNA SENSING DEVICES

(71) Applicant: QUALCOMM Incorporated, San Diego, CA (US)

(72) Inventors: Yong Ju Lee, San Diego, CA (US); Vladimir Aparin, San Diego, CA (US)

(73) Assignee: Qualcomm Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/141,927

(22) Filed: Sep. 25, 2018

(65) Prior Publication Data

US 2019/0024254 A1    Jan. 24, 2019

Related U.S. Application Data

(63) Continuation of application No. 15/587,373, filed on May 4, 2017, now Pat. No. 10,081,879.

(Continued)

(51) Int. Cl.
| | | |
|---|---|---|
| C25D 7/12 | (2006.01) |
| G01N 33/487 | (2006.01) |
| G01N 27/30 | (2006.01) |
| H01L 21/285 | (2006.01) |
| C25D 3/46 | (2006.01) |
| C25D 5/48 | (2006.01) |

(Continued)

(52) U.S. Cl.
CPC ............ C25D 7/123 (2013.01); C25D 3/46 (2013.01); C25D 5/48 (2013.01); G01N 27/301 (2013.01); G01N 27/4145 (2013.01); G01N 27/4146 (2013.01); G01N 27/44791 (2013.01); G01N 33/48721 (2013.01); H01L 21/2855 (2013.01)

(58) Field of Classification Search
None
See application file for complete search history.

(56) References Cited

U.S. PATENT DOCUMENTS

| | | |
|---|---|---|
| 8,262,879 B2 | 9/2012 | Oliver |
| 8,453,319 B2 | 6/2013 | Zhang |

(Continued)

OTHER PUBLICATIONS

International Search Report and Written Opinion—PCT/US2017/031377—ISA/EPO—Sep. 22, 2017.

(Continued)

*Primary Examiner* — Angel Roman
(74) *Attorney, Agent, or Firm* — Muncy, Geissler, Olds & Lowe, P.C.

(57) ABSTRACT

Techniques for increasing the lifespan of a nanopore DNA sensing device are disclosed. A related DNA sensing device may be formed by a process comprising forming a first electrode, forming a second electrode, disposing the first electrode and second electrode within an insulator, and disposing a lipid bilayer having a nanopore between the first electrode and second electrode. The forming of the second electrode may comprise forming a silver (Ag) layer, pressing a mold into the Ag layer to form a pattern in the Ag layer, removing the mold from the Ag layer, and exposing the Ag layer to an electrolyte.

20 Claims, 8 Drawing Sheets

Related U.S. Application Data

(60) Provisional application No. 62/332,670, filed on May 6, 2016.

(51) Int. Cl.
*G01N 27/414* (2006.01)
*G01N 27/447* (2006.01)

(56) References Cited

U.S. PATENT DOCUMENTS

| | | | |
|---|---|---|---|
| 8,628,649 | B2 | 1/2014 | Lindsay et al. |
| 9,263,519 | B2 | 2/2016 | Lal et al. |
| 10,081,879 | B2 * | 9/2018 | Lee .................. C25D 3/46 |
| 2002/0029588 | A1 | 3/2002 | Themont et al. |
| 2002/0121439 | A1 | 9/2002 | Crumly et al. |
| 2003/0208248 | A1 | 11/2003 | Carter et al. |
| 2006/0116001 | A1 | 6/2006 | Wang |
| 2009/0195963 | A1 | 8/2009 | Masuda et al. |
| 2010/0035260 | A1 | 2/2010 | Olasagasti et al. |
| 2013/0149605 | A1 | 6/2013 | Kakehata et al. |
| 2013/0164612 | A1 | 6/2013 | Tanemura et al. |
| 2013/0236781 | A1 | 9/2013 | Oguni et al. |
| 2014/0342128 | A1 | 11/2014 | Haynes et al. |
| 2015/0104567 | A1 | 4/2015 | Lee et al. |
| 2016/0251699 | A1 | 9/2016 | Alam et al. |
| 2016/0284891 | A1 | 9/2016 | Jung et al. |
| 2017/0321342 | A1 | 11/2017 | Lee et al. |
| 2018/0095067 | A1 * | 4/2018 | Huff .................. G01N 33/54326 |

OTHER PUBLICATIONS

Partial International Search Report—PCT/US2017/031377—ISA/EPO—Aug. 1, 2017.

Rahman M.M., et al., "Fabrication of Patterned Integrated Electrochemical Sensors", Hindawi Publishing Corporation Journal of Nanotechnology, vol. 2015, pp. 1-14.

Shim J.S., et al., "Formation of Lipid Bilayers Inside Microfluidic Channel Array for Monitoring Membrane-Embedded Nanopores of phi29 DNA Packaging Nanomotor", Biomedical Microdevices, Kluwer Academic Publishers, vol. 14, No. 5, Jul. 7, 2012, XP035113958, ISSN: 1572-8781, DOI: 10.1007/S10544-012-9671-6, pp. 921-928.

* cited by examiner

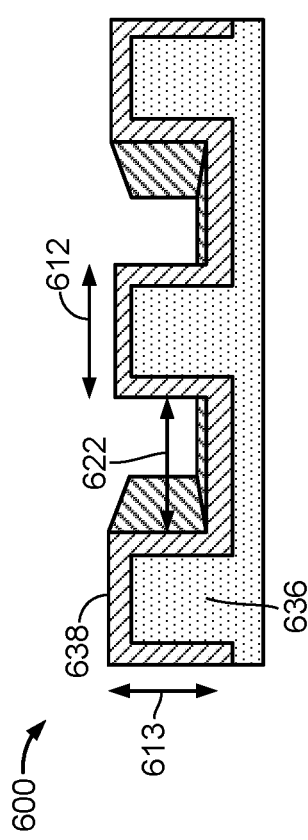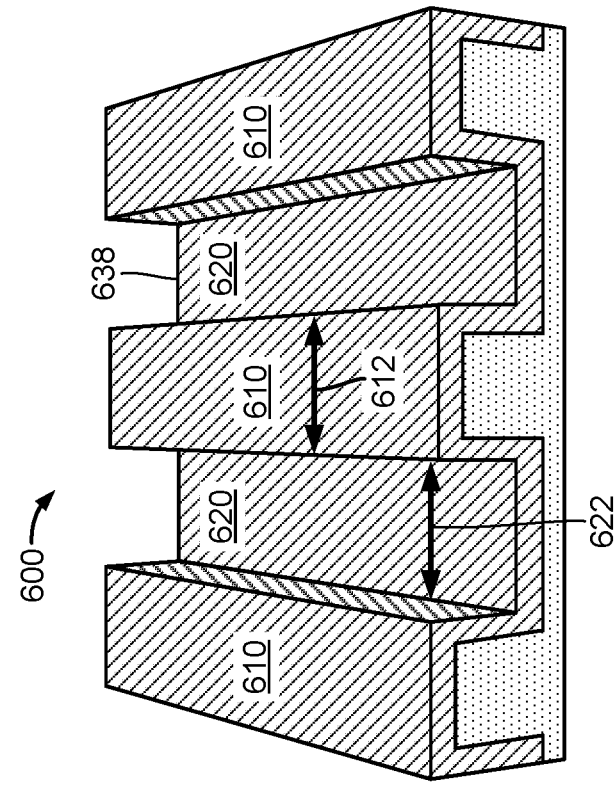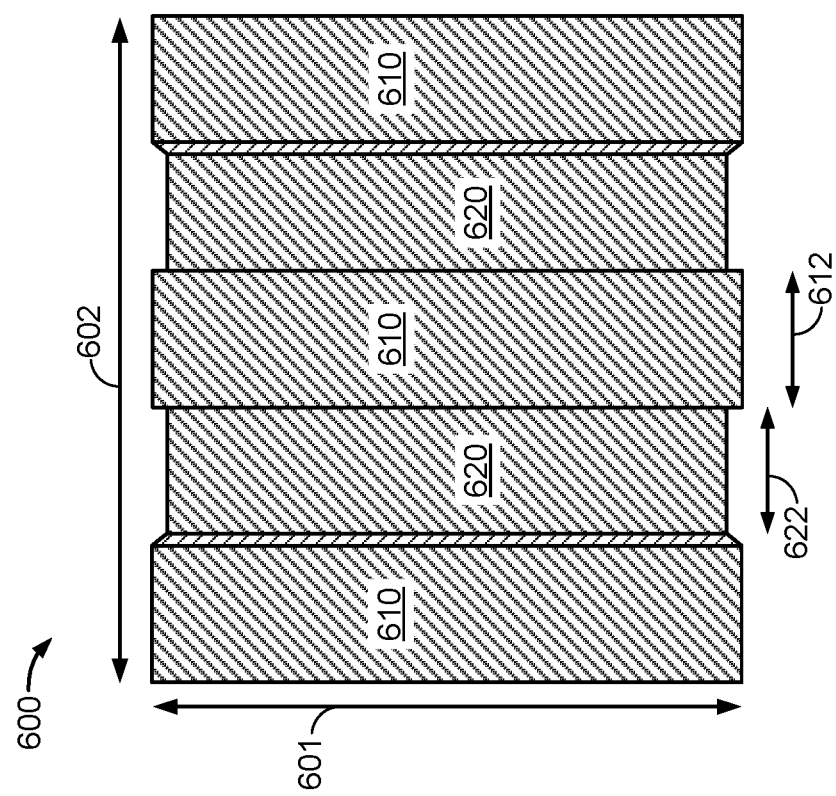

US 10,538,853 B2

METHOD AND APPARATUS FOR INCREASING A LIFESPAN OF NANOPORE-BASED DNA SENSING DEVICES

CROSS-REFERENCE TO RELATED APPLICATIONS

The present application for patent is a continuation of U.S. application Ser. No. 15/587,373, entitled "Method and Apparatus For Increasing a Lifespan of Nanopore-based DNA Sensing Devices", filed May 4, 2017, which claims the benefit of U.S. Provisional Application No. 62/332,670, entitled "Method and Apparatus For Increasing a Lifespan of Nanopore-based DNA Sensing Devices", filed May 6, 2016, assigned to the assignee hereof, and expressly incorporated herein by reference in its entirety, assigned to the assignee hereof, and expressly incorporated herein by reference in its entirety.

INTRODUCTION

Aspects of this disclosure relate generally to sensing devices for deoxyribonucleic acid (DNA), and more particularly to methods and apparatuses for increasing the lifetime of nanopore-based DNA sensing devices.

DNA, sometimes referred to as the "blueprint of life", is a molecule that stores biological information. The structure of DNA, famously discovered by James Watson and Francis Crick, consists of two strands of biopolymer, coiled around one another to form a double helix. Each strand is a polynucleotide that includes a plurality of nucleotides, for example, cytosine ("C"), guanine ("G"), adenine ("A"), and thymine ("T"). Each nucleotide in a first strand of DNA may be bonded to a paired nucleotide in the second strand, thereby forming a base pair. Generally, cytosine and guanine are paired to form a "G-C" or "C-G" base pair, and adenine and thymine are paired to form an "A-T" or "T-A" base pair.

Although the structure of DNA is now known, new methods for analyzing individual DNA molecules are still being developed. Generally, the analysis includes 'reading' the nucleotide sequence of a particular DNA strand. In one method, known as nanopore DNA sequencing, a nanopore is immersed in a conductive fluid, and a voltage is applied across the nanopore. As a result, ions are conducted through the nanopore, thereby generating a measurable electric current. A DNA strand is then transmitted through the nanopore, one nucleotide at a time. The presence of a nucleotide within the nanopore disrupts the conduction of the ions, thereby causing a change in the electric current. Moreover, the change in electrical current due to a particular nucleotide differs from the change in electrical current due to other nucleotides. Accordingly, an entire DNA strand can be transmitted through the nanopore and each nucleotide in the strand can be identified based on the change in current.

As nanopore DNA sequencing improves, new challenges are presented. For example, the electrodes used to draw ions through the nanopore may wear out due to chemical changes. As a result, new technologies are needed for increasing the lifespan of nanopore DNA sensing devices.

SUMMARY

The following summary is an overview provided solely to aid in the description of various aspects of the disclosure and is provided solely for illustration of the aspects and not limitation thereof.

In one example, a method of forming a DNA sensing device is disclosed. The method may include, for example, forming a first electrode, forming a second electrode, wherein forming the second electrode comprises forming a silver (Ag) layer, pressing a mold into the Ag layer to form a pattern in the Ag layer, removing the mold from the Ag layer, and exposing the Ag layer to an electrolyte, disposing the first electrode and second electrode within an insulator, disposing a lipid bilayer having a nanopore between the first electrode and second electrode.

In another example, a method of forming an electrode is disclosed. The method may include, for example, forming a silver (Ag) layer, pressing a mold into the Ag layer to form a pattern in the Ag layer, removing the mold from the Ag layer, and exposing the Ag layer to an electrolyte.

BRIEF DESCRIPTION OF THE DRAWINGS

The accompanying drawings are presented to aid in the description of various aspects of the disclosure and are provided solely for illustration of the aspects and not limitation thereof.

FIG. 6A generally illustrates an electrode in accordance with an aspect of the disclosure from a topographic view.

FIG. 6B generally illustrates the electrode of FIG. 6A from a cross-sectional view.

FIG. 6C generally illustrates the electrode of FIG. 6A from a tilted cross-sectional view.

DETAILED DESCRIPTION

The present disclosure relates generally to a method and apparatus for increasing the lifespan of a nanopore DNA sensing device.

More specific aspects of the disclosure are provided in the following description and related drawings directed to various examples provided for illustration purposes. Alternate aspects may be devised without departing from the scope of the disclosure. Additionally, well-known aspects of the disclosure may not be described in detail or may be omitted so as not to obscure more relevant details.

Those of skill in the art will appreciate that the information and signals described below may be represented using any of a variety of different technologies and techniques. For example, data, instructions, commands, information, signals, bits, symbols, and chips that may be referenced throughout the description below may be represented by voltages, currents, electromagnetic waves, magnetic fields or particles, optical fields or particles, or any combination thereof, depending in part on the particular application, in part on the desired design, in part on the corresponding technology, etc.

Further, many aspects are described in terms of sequences of actions to be performed by, for example, elements of a computing device. It will be recognized that various actions described herein can be performed by specific circuits (e.g., Application Specific Integrated Circuits (ASICs)), by program instructions being executed by one or more processors, or by a combination of both. In addition, for each of the aspects described herein, the corresponding form of any such aspect may be implemented as, for example, "logic configured to" perform the described action.

Figure 1:
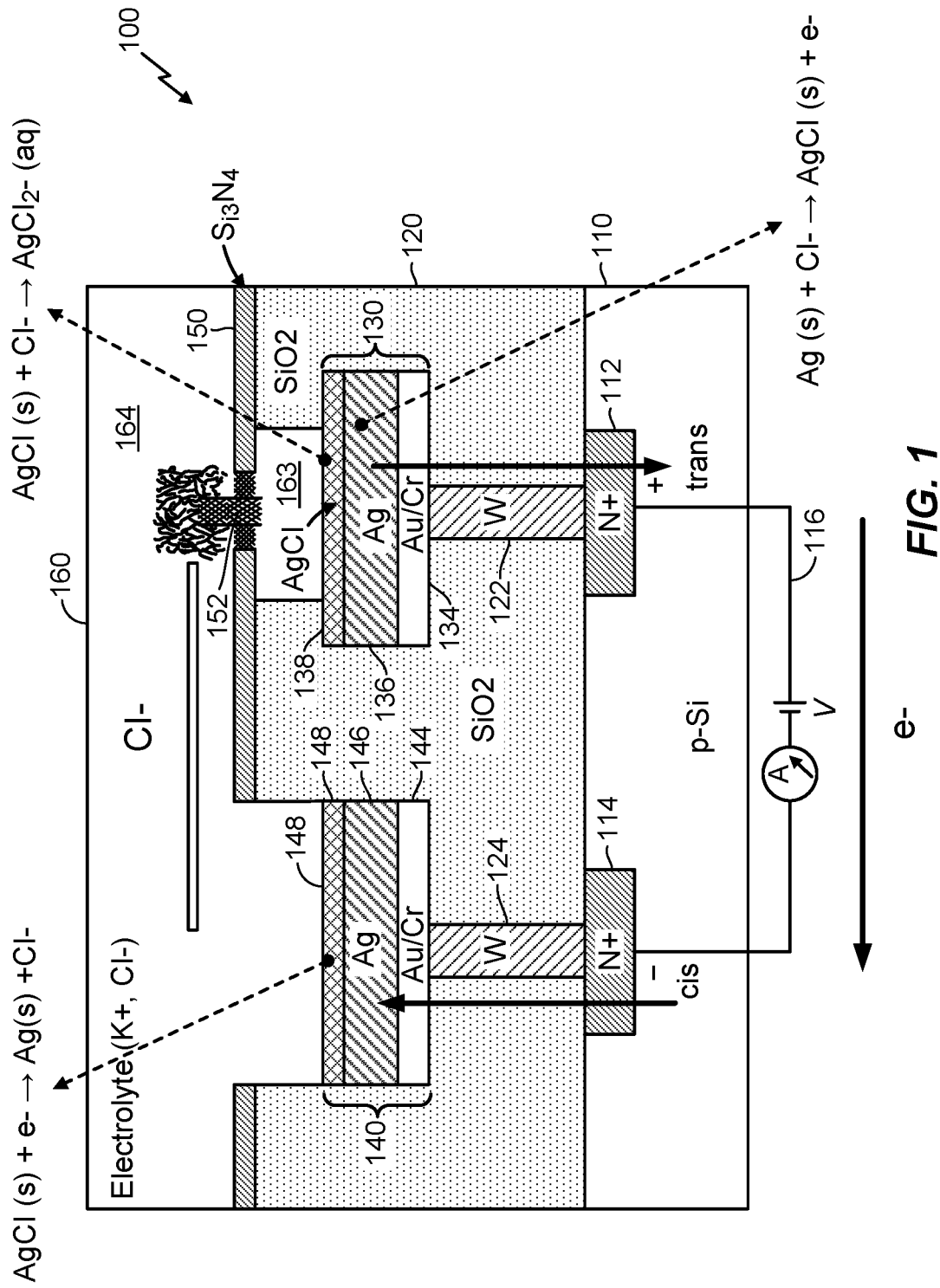
FIG. 1 generally illustrates a nanopore DNA sensing device in accordance with an aspect of the disclosure.

FIG. 1 generally illustrates a nanopore DNA sensing device 100 in accordance with an aspect of the disclosure.

The nanopore DNA sensing device 100 includes a semiconductor device 110 having a first semiconductor contact area 112 and a second semiconductor contact area 114. As an example, the semiconductor device 110 may include p-doped silicon and the semiconductor contact areas 112 and 114 may include n-doped silicon and p-doped silicon. However, it will be understood that any suitable material may be selected. The nanopore DNA sensing device 100 may further include a conductor 116. The conductor 116 may be used to apply a voltage V between the first semiconductor contact area 112 and the second semiconductor contact area 114. In the arrangement of FIG. 1, the first semiconductor contact area 112 constitutes a trans-electrode and the second semiconductor contact area 114 constitutes a cis-electrode, but it will be understood that the polarity of the voltage V may be reversed. Moreover, an electrical current i through the conductor 116 may be, for example, detected, amplified, and/or measured. The changes in the current i may be used to determine a DNA sequence, as will be discussed in greater detail below.

The nanopore DNA sensing device 100 further includes an insulator 120. The insulator 120 may include a first via 122 and a second via 124 in contact with the first semiconductor contact area 112 and the second semiconductor contact area 114, respectively. As an example, the insulator 120 may include silicon dioxide (SiO2), however, it will be understood that any suitable material may be selected. The first via 122 and the second via 124 may include, for example, tungsten (W), however, it will be understood that any suitable material may be selected.

The insulator 120 further includes a first electrode 130 and a second electrode 140 in contact with the first via 122 and the second via 124, respectively. The first electrode 130 may include an adhesion/diffusion layer 134, a conductive layer 136, and a surface layer 138. Similarly, the second electrode 140 may include an adhesion/diffusion layer 144, a conductive layer 146, and a surface layer 148.

As an example, the adhesion/diffusion layer 134 may include a chromium (Cr) adhesion layer in contact with the first via 122 and a gold (Au) diffusion layer between the conductive layer 136 and the Cr adhesion layer. Additionally or alternatively, the adhesion/diffusion layer 134 may include titanium nitride (TiN). It will be understood that any other suitable material may be selected to fabricate the adhesion/diffusion layer 134. Like the adhesion/diffusion layer 134, the adhesion/diffusion layer 144 may include Cr, Au, TiN, any other suitable material, or any combination thereof.

The conductive layer 136 may include silver (Ag), however, it will be understood that any suitable material may be selected. Moreover, the surface layer 138 may include silver chloride (AgCl), however, it will be understood that any suitable material may be selected. Like the conductive layer 136 and surface layer 138, the conductive layer 146 and surface layer 148 may include Ag, AgCl, any other suitable material, or any combination thereof.

The nanopore DNA sensing device 100 further includes a separation layer 150 having a nanopore 152 embedded therein. As an example, the separation layer 150 may include silicon nitride (Si3N4) and/or a lipid bilayer. However, it will be understood that any suitable material may be selected.

The nanopore DNA sensing device 100 further includes a chamber 160. The chamber 160 may hold a conductive fluid therein. The conductive fluid may include, for example, one or more electrolytes, for example, chlorine electrolyte (Cl−), potassium electrolyte (K+), hydrogen electrolyte (H+), or any other suitable material. The conductive fluid within the chamber 160 may be divided by the separation layer 150 into a first subchamber 163 and a second subchamber 164. Fluid in the first subchamber 163 may be in contact with the surface layer 138 of the electrode 130, and fluid in the second subchamber 164 may be in contact with the surface layer 148 of the electrode 140. In the nanopore DNA sensing device 100 of FIG. 1, the first subchamber 163 may be a positive chamber (i.e., associated with a trans-electrode) and the second subchamber 164 may be a negative chamber (i.e., associated with a cis-electrode), but it will be understood that the polarity of the chambers may be reversed.

Figure 2:
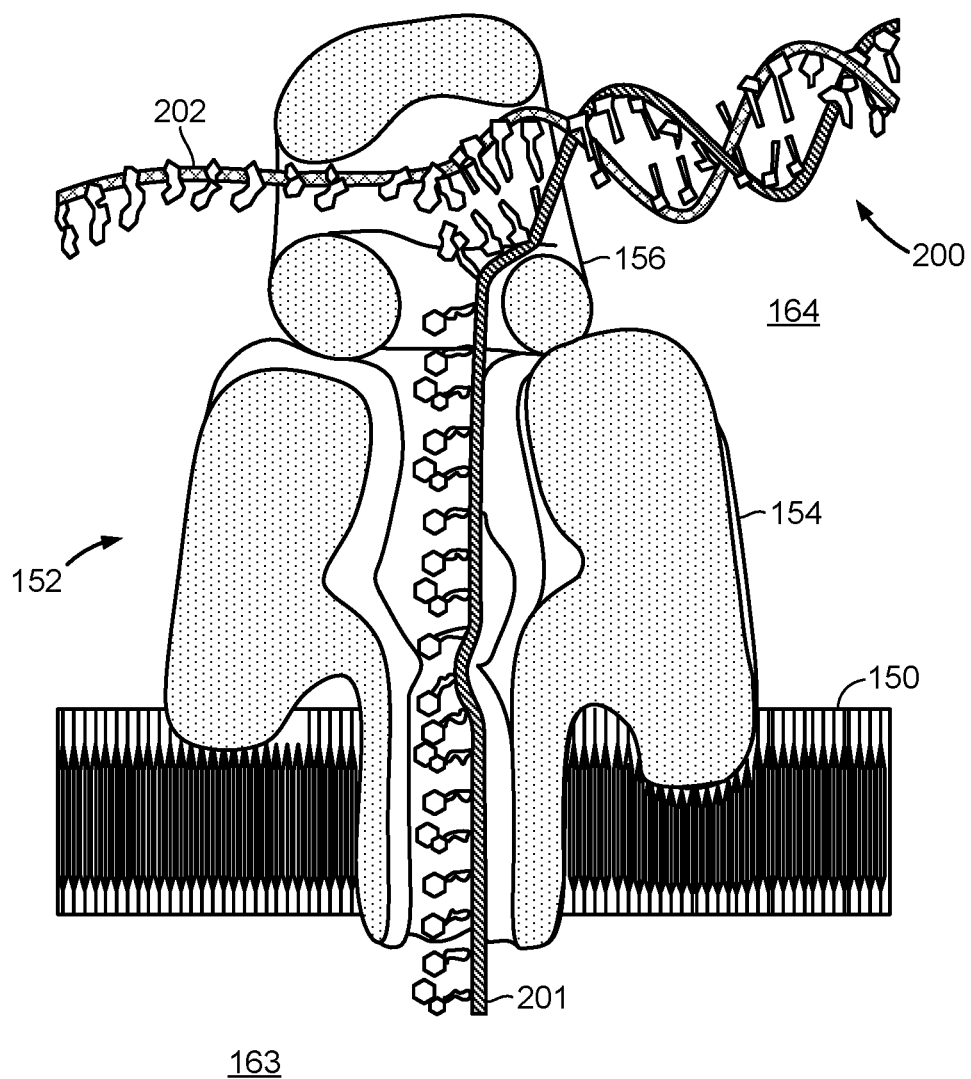
FIG. 2 generally illustrates a detail of a nanopore in accordance with an aspect of the disclosure.

FIG. 2 generally illustrates a detail of the nanopore 152 of FIG. 1 in accordance with an aspect of the disclosure. As noted above, the nanopore 152 may be embedded in the separation layer 150, and the separation layer 150 may separate the first subchamber 163 from the second subchamber 164. As noted previously, the separation layer 150 may include a lipid bilayer.

The nanopore 152 may include, for example, a translocator 154 and an assembler 156. The translocator 154 permits passage of conductive fluid between the first subchamber 163 and the second subchamber 164. For example, if the second subchamber 164 is negatively charged and the first subchamber 163 is positively charged, then negative ions (for example, Cl−) may pass from the second subchamber 164 to the first subchamber 163 via the translocator 154. In some implementations, the translocator 154 may include alpha hemolysin.

The assembler 156 may separate a double-stranded DNA molecule 200 into a first DNA strand 201 and a second DNA strand 202 and/or combine the first DNA strand 201 and the second DNA strand 202 into the double-stranded DNA molecule 200. In some implementations, the assembler 156 may include DNA polymerase.

FIG. 2 may illustrate either separation or combination of the double-stranded DNA molecule 200. For example, the double-stranded DNA molecule 200 may move from the second subchamber 164 into the assembler 156, where it is separated by the assembler 156 into the first DNA strand 201 and the second DNA strand 202. The first DNA strand 201 may be led into the translocator 154 and translocated across the separation layer 150, from the second subchamber 164 to the first subchamber 163. As another example, the first DNA strand 201 may be drawn from the first subchamber 163 through the translocator 154 and into the assembler 156, where it is combined with the second DNA strand 202 into the double-stranded DNA molecule 200. The double-stranded DNA molecule 200 may then be moved into the second subchamber 164.

In some implementations, the following method may be used to perform DNA sequencing using the nanopore DNA sensing device 100 of FIG. 1 and the nanopore 152 of FIG. 2. First, a voltage may be applied to the first semiconductor contact area 112 and the second semiconductor contact area 114 via the conductor 116. As a result, a positive charge appears on the first electrode 130 and a negative charge appears on the second electrode 140.

As an example, the second electrode 140 may include a surface layer 148 including AgCl and a conductive layer 146 including Ag. When the voltage V is applied (such that the second electrode 140 is negatively charged), the AgCl in the second electrode 140 may be converted into Ag and chlorine electrolytes, i.e., $AgCl(s)+e- \rightarrow Ag(s)+Cl-$. As the second electrode 140 generates Cl- ions, the second subchamber 164 may become negatively charged.

Moreover, the first electrode 130 may include a surface layer 138 including AgCl and a conductive layer 136 including Ag. When the voltage V is applied (such that the first electrode 130 is positively charged), the Ag in the first electrode 130 may combine with Cl- ions in the first subchamber 163, i.e., $Ag(s)+Cl- \rightarrow AgCl(s)+e-$. As the first electrode 130 combines Cl- ions into AgCl, the first subchamber 163 may become positively charged.

As a result, ions in the chamber 160 may have a tendency to flow toward either the first subchamber 163 (which is positively charged) or the second subchamber 164 (which is negatively charged). For example, Cl- ions in the chamber 160 (including Cl- ions generated at the second electrode 140) may have a tendency to flow toward the positively-charged first subchamber 163.

Moreover, as the first electrode generates electrons e- and the second electrode 140 absorbs electrons e-, the electrical current i flowing through the conductor 116 may also increase.

Because Cl- ions may have a tendency to flow toward the positively-charged first subchamber 163, the Cl- ions may translocate across the separation layer 150 via the nanopore 152. However, the nanopore 152 may also be configured to translocate DNA (for example, the first DNA strand 201, as shown in FIG. 2).

As the first DNA strand 201 shown in FIG. 2 is being translocated, it may impede the flow of Cl- ions through the nanopore 152. As a result, the current i may be reduced due to the translocation of the first DNA strand 201. Moreover, different types of nucleotide may have different effects on the flow of Cl- ions through the nanopore 152.

Accordingly, as different types of nucleotide pass through the nanopore 152, different quantities of Cl- ions may pass through the nanopore 152, and a different electrical current i may be measured on the conductor 116. For example, a C nucleotide may cause a current iC, an A nucleotide may cause a current iA, a T nucleotide may cause a current iT, and a G nucleotide may cause a small current iG. As the first DNA strand 201 passes through the nanopore 152, the nanopore DNA sensing device 100 will generate a current waveform i(t) that indicates the sequence of nucleotides in the first DNA strand 201.

Figures 3A, 3B:
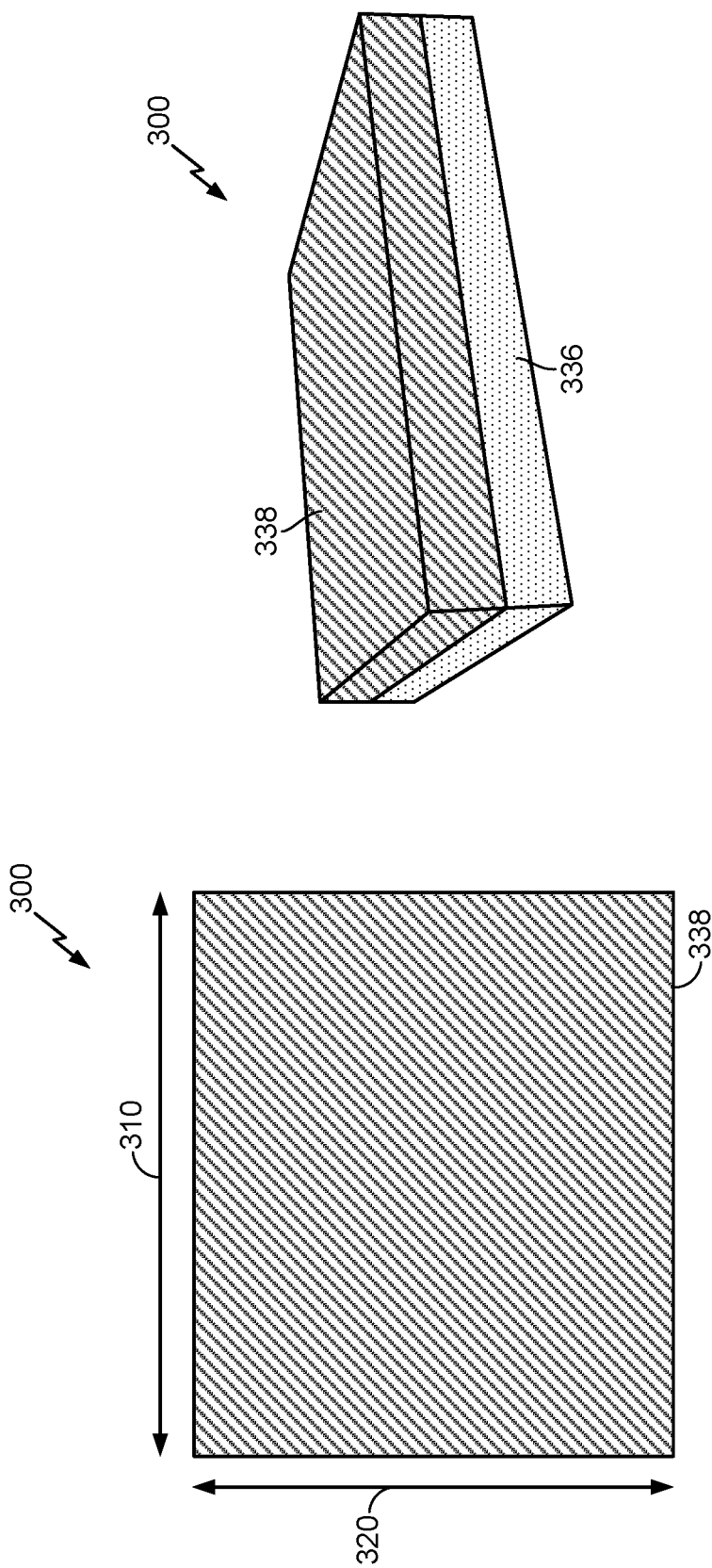
FIG. 3A depicts a topographic view of a conventional electrode.
FIG. 3B depicts a tilted view of the conventional electrode of FIG. 3A.

FIGS. 3A-3B generally illustrate portions of a conventional electrode 300. FIG. 3A depicts a topographic view of the electrode 300, whereas FIG. 3B depicts a tilted view of the electrode 300. The electrode 300 may include a surface layer 338 and a conductive layer 336. The surface layer 338 and the conductive layer 336 may be analogous to the surface layer 138 and the conductive layer 136, respectively, depicted in FIG. 1. The electrode 300 may have a length 310 and a width 320.

If the electrode 300 is included in the nanopore DNA sensing device 100, then it will be disposed on the insulator 120 such that the surface layer 338 is in contact with the chamber 160. The footprint of the electrode 300 may be substantially equal to the length 310 multiplied by the width 320. For example, if the length 310 has a value of L and the width 320 has a value of W, then the footprint of the electrode 300 may be equal to LW.

Similarly, the surface layer 338 of the conventional electrode 300 may have a surface area that is substantially equal to the length 310 multiplied by the width 320. For example, if the length 310 has a value of L and the width 320 has a value of W, then the surface area of the surface layer 338 may be equal to LW. It will be understood that if the electrode 300 is included in the nanopore DNA sensing device 100, then the surface area of the surface layer 338 will be substantially equal to the footprint of the electrode 300.

The lifespan of the nanopore DNA sensing device 100 may be limited based on the surface area LW of the electrode 300. For example, in the conventional electrode 300, the surface layer 338 may be made of AgCl and the conductive layer 336 may be made of Ag. If the electrode 300 is used as a trans-electrode, then the nanopore DNA sensing device 100 may lose sensitivity as the conductive layer 336 absorbs ions. In particular, over the lifespan of the nanopore DNA sensing device 100, the volume of AgCl may increase as Cl- ions are absorbed from the chamber 160 and combined with the Ag. Because the volume of AgCl increases at the expense of the volume of Ag, the nanopore DNA sensing device 100 may lose effectiveness (for example, reduced sensitivity, etc.).

However, as will be discussed in greater detail below, if the surface area of the surface layer can be increased, then the lifespan of the nanopore DNA sensing device 100 may also be increased. Moreover, if the surface area of the surface layer can be increased without also increasing the size of the footprint of the electrode, then the lifespan of the nanopore DNA sensing device 100 can be increased without increasing the overall size of the nanopore DNA sensing device 100.

Figure 4:
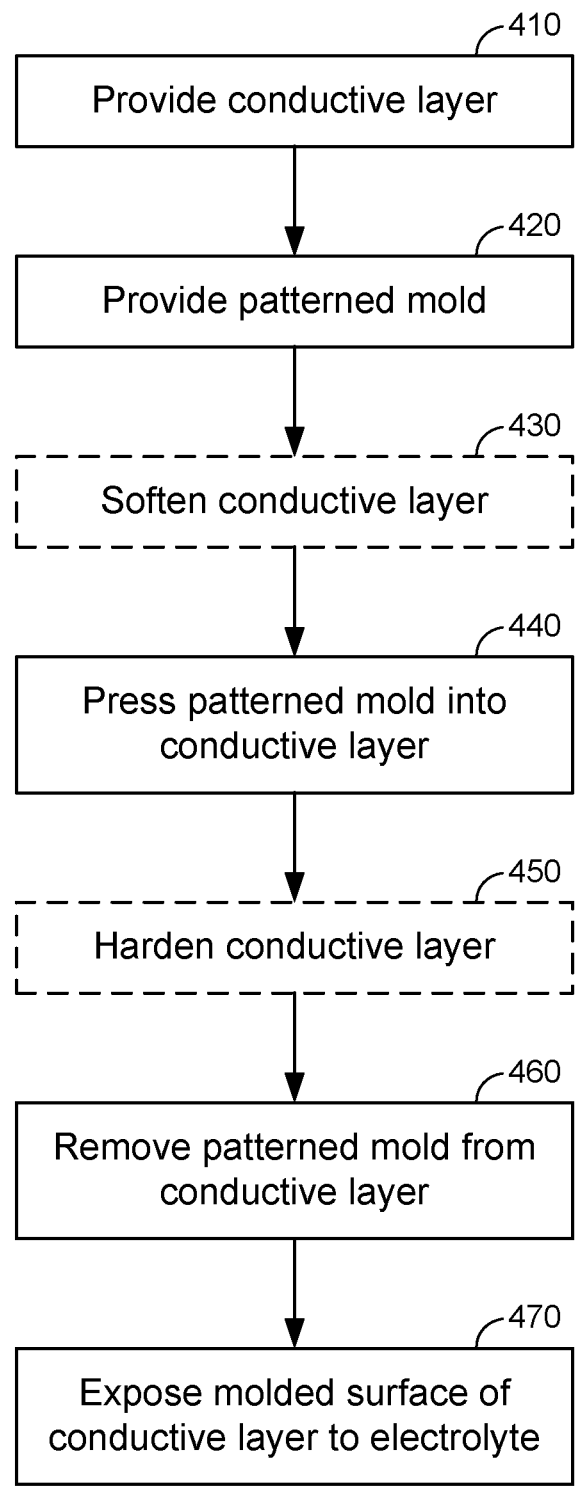
FIG. 4 generally illustrates a method for fabricating an electrode in accordance with an aspect of the disclosure.

FIG. 4 generally illustrates a method 400 for fabricating an electrode in accordance with an aspect of the disclosure. The electrode may be included, for example, in the nanopore DNA sensing device 100 of FIG. 1. As will be appreciated for the following discussion, in an electrode fabricated in accordance with the method 400, the size of the surface area of the surface layer may be greater than the footprint of the electrode.

At 410, a conductive layer is provided. The conductive layer may be analogous to, for example, the conductive layer 136 and/or the conductive layer 146 depicted in FIG. 1. The conductive layer may have a length in a length direction and a width in a width direction. The conductive layer may be substantially uniform in a depth direction. For example, the conductive layer may be flat, for example, formed as a planar surface. The conductive layer may include, for example, Ag. The layer provided at 410 may be formed via electroplating or physical vapor deposition (PVD).

At 420, a patterned mold is provided. The patterned mold may include a patterned portion have a three-dimensional pattern. For example, the patterned portion of the patterned mold may have a length, a width, and a depth. In some implementations, the width of the patterned portion may be substantially equal to the width of the conductive layer and a length of the patterned portion may be substantially equal to the length of the conductive layer provided at 410. The patterned mold may be substantially non-uniform in a depth direction, for example, formed as a non-planar surface. The patterned mold may include, for example, a polymer or any other suitable material.

At 430, the conductive layer provided at 410 is optionally softened. The softening at 430 may be performed by, for example, heating the conductive layer. If the conductive layer includes Ag, then the softening at 430 may include heating the conductive layer to a temperature of between one-hundred-fifty degrees Celsius and four-hundred degrees Celsius.

At 440, the patterned mold provided at 420 is pressed into the conductive layer provided at 410. The pressing at 440 may cause deformation of the conductive layer. If the conductive layer is softened at 430, then the pressing at 440 may be performed while the conductive layer is in a softened state. The patterned mold may be aligned with the conductive layer such that the width direction of the patterned mold and the width direction of the conductive layer are substantially parallel. Moreover, the patterned mold may be aligned with the conductive layer such that the length direction of the patterned mold and the length direction of the conductive layer are substantially parallel. Moreover, the patterned mold may be pressed, at least in part, in the depth direction of the patterned mold.

At 450, the conductive layer provided at 410 is optionally hardened. The hardening at 450 may be performed by, for example, cooling the conductive layer. If the conductive layer includes Ag, then the hardening at 450 may include cooling the conductive layer to below one hundred and fifty degrees Celsius.

At 460, the patterned mold is removed from the conductive layer. If the conductive layer is hardened at 450, then the removing at 460 may be performed while the conductive layer is in a hardened state. After the removing at 460, the conductive layer may have a molded surface that takes the opposite shape of the mold, for example, formed as a non-planar molded surface. In particular, the molded surface of the conductive layer may be substantially non-uniform in the depth direction.

At 470, a molded surface of the conductive layer is exposed to an electrolyte. The exposing at 470 may result in the forming of a surface layer analogous to, for example, the surface layer 138 and/or the surface layer 148 depicted in FIG. 1. The surface layer may be substantially non-uniform in the depth direction. The electrolyte may be, for example, Cl–.

FIGS. 5A-5D generally illustrate, in various stages of fabrication, an electrode 500 fabricated in accordance with the method 400 of FIG. 4.

Figure 5A:
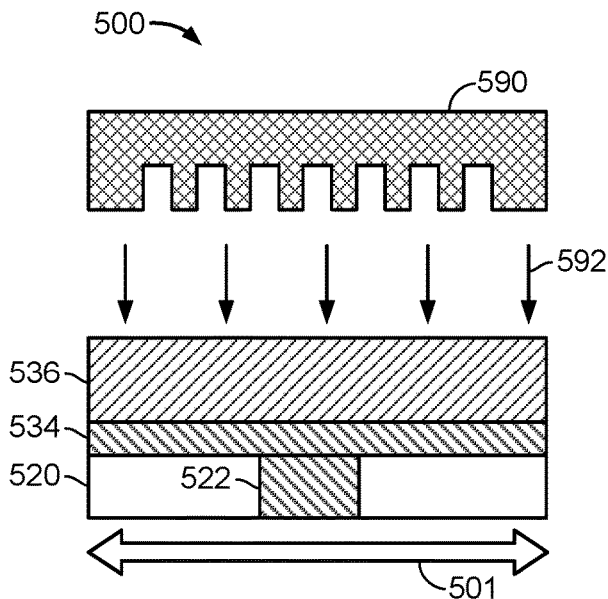
FIG. 5A generally illustrates an electrode fabricated in accordance with the method of FIG. 4 in a first stage of fabrication.

FIG. 5A generally illustrates an electrode 500 fabricated in accordance with the method of 400 prior to the pressing at 440. FIG. 5A depicts an insulator 520 (analogous to, for example, the insulator 120 depicted in FIG. 1), a via 522 (analogous to, for example, the via 122 and/or the via 124 depicted in FIG. 1), an adhesion/diffusion layer 534 (analogous to, for example, the adhesion/diffusion layer 134 and/or the adhesion/diffusion layer 144 depicted in FIG. 1), and a conductive layer 536 (analogous to, for example, the conductive layer 136 and/or the conductive layer 146 depicted in FIG. 1). The electrode 500 may have a footprint 501. Although only one dimension of the two-dimensional footprint 501 is shown in FIG. 5A, it will be understood that the footprint 501 may have a length L as well as width W. Moreover, it will be understood from FIG. 5A that the size of the footprint 501 is substantially equal to the surface area of the conductive layer 536 (LW).

FIG. 5A further depicts a patterned mold 590 having a patterned portion that is substantially non-uniform in a depth direction 592. After providing the conductive layer 536 and the patterned mold 590 (as at 410 and 420 in FIG. 4), the conductive layer 536 may be optionally softened (as at 430 in FIG. 4). FIG. 5A further depicts a depth direction 592 in which the patterned mold 590 may be pressed (as at 440 in FIG. 4).

Figure 5B:
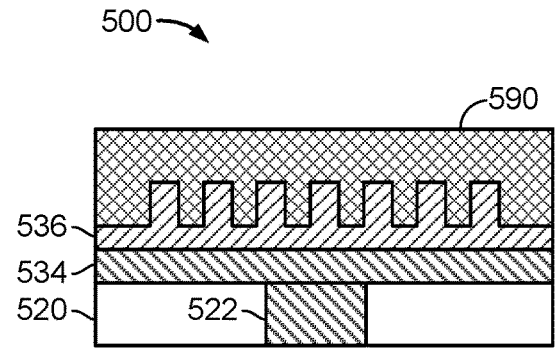
FIG. 5B generally illustrates an electrode fabricated in accordance with the method of FIG. 4 in a second stage of fabrication.

FIG. 5B generally illustrates an electrode 500 fabricated in accordance with the method of 400 after the pressing of the patterned mold 590 into the conductive layer 536 (as at 440 in FIG. 4). Accordingly, a patterned portion of the patterned mold 590 is in contact with the conductive layer 536. Because the patterned portion of the patterned mold 590 is substantially non-uniform in a depth direction, pressing of the patterned mold 590 against the conductive layer 536 causes the conductive layer 536 to take the opposite shape of the patterned portion of the patterned mold 590. After pressing the conductive layer 536 (as at 440 in FIG. 4), the conductive layer 536 may be optionally hardened (as at 450 in FIG. 4).

Figure 5C:
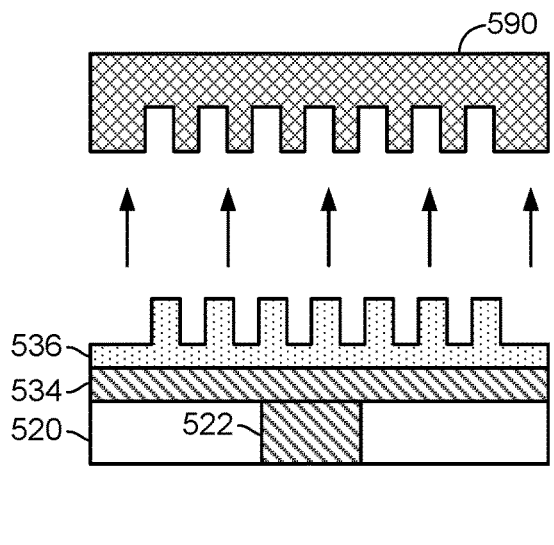
FIG. 5C generally illustrates an electrode fabricated in accordance with the method of FIG. 4 in a third stage of fabrication.

FIG. 5C generally illustrates an electrode 500 fabricated in accordance with the method of 400 after the removing of the patterned mold 590 from the conductive layer 536 (as at 460 in FIG. 4). As can be understood from FIG. 5C, the conductive layer 536 may maintain the opposite shape of the patterned portion of the patterned mold 590, even after the patterned mold 590 is removed. In particular, the conductive layer 536 may be substantially non-uniform in the depth direction.

Figure 5D:
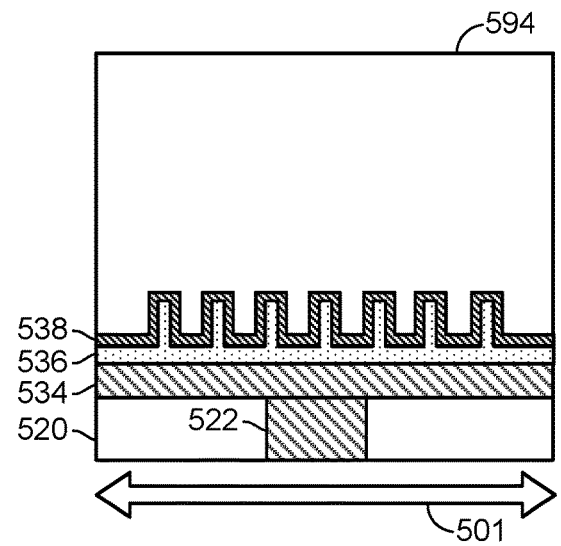
FIG. 5D generally illustrates an electrode fabricated in accordance with the method of FIG. 4 in a fourth stage of fabrication.

FIG. 5D generally illustrates an electrode 500 fabricated in accordance with the method of 400 after the exposing of the conductive layer 536 to an electrolyte 594 (as at 470 in FIG. 4). The electrolyte 594 may cause a surface layer 538 to form on a surface of the conductive layer 536. For example, if the conductive layer 536 include Ag and the electrolyte 594 includes Cl–, then the surface layer 538 depicted in FIG. 5D may include AgCl.

Although only one dimension of the two-dimensional footprint 501 is shown in FIG. 5D, it will be understood that the size of the footprint 501 as depicted in FIG. 5D is substantially equal to the size of the footprint 501 as depicted in FIG. 5A (LW). However, it will be further understood that the surface area of the surface layer 538 has increased, and is now greater than the size of the footprint 501. This is due to the fact that the surface layer 538 is substantially non-uniform in the depth direction.

FIGS. 6A-6C generally illustrate an electrode 600 fabricated in accordance with the method of 400. FIG. 6A generally illustrates the electrode 600 from a topographic view. FIG. 6B generally illustrates the electrode 600 from a cross-sectional view. FIG. 6C generally illustrates the electrode 600 from a tilted cross-sectional view.

The electrode 600 includes a conductive layer 636 and a surface layer 638. The size of the footprint of the electrode 600 is defined as an electrode length 601 of the electrode 600 multiplied by an electrode width 602 of the electrode 600.

The electrode 600 further includes one or more fins 610 and one or more trenches 620. Each fin 610 and each trench 620 may have a length that is equal to the electrode length 601. However, as can be seen from FIG. 6A, the fin width 612 may be less than the electrode width 602. Moreover, the trough width 622 may be less than the electrode width 602.

Each fin 610 may also have a fin depth 613. The fin depth 613 may be equal to a distance in a depth direction between a top surface of the fin 610 and a top surface of an adjacent trench 620.

As can be understood from FIGS. 6A-6C, the surface area of the surface layer 638 exceeds the size of the footprint of the electrode 600. As an example, consider a scenario wherein the electrode 600 has an electrode length 601 equal to ten micrometers (10 µm) and an electrode width 602 equal to 10 µm. In this scenario, the footprint of the electrode 600 will be equal to one hundred square micrometers (100 µm2). If the surface layer 638 were uniform in a depth direction, then the surface area of the surface layer 638 would also be equal to 100 µm2. However, because the surface layer 638 is non-uniform in a depth direction, the surface area of the surface layer 638 will be greater than 100 µm2. For example, given a fin width 612 of 2 µm, a trough width 622 of 2 µm, and a fin depth 613 of 3 µm, the surface area of the surface layer 638 may be approximately 220 µm2.

Figure 7C:
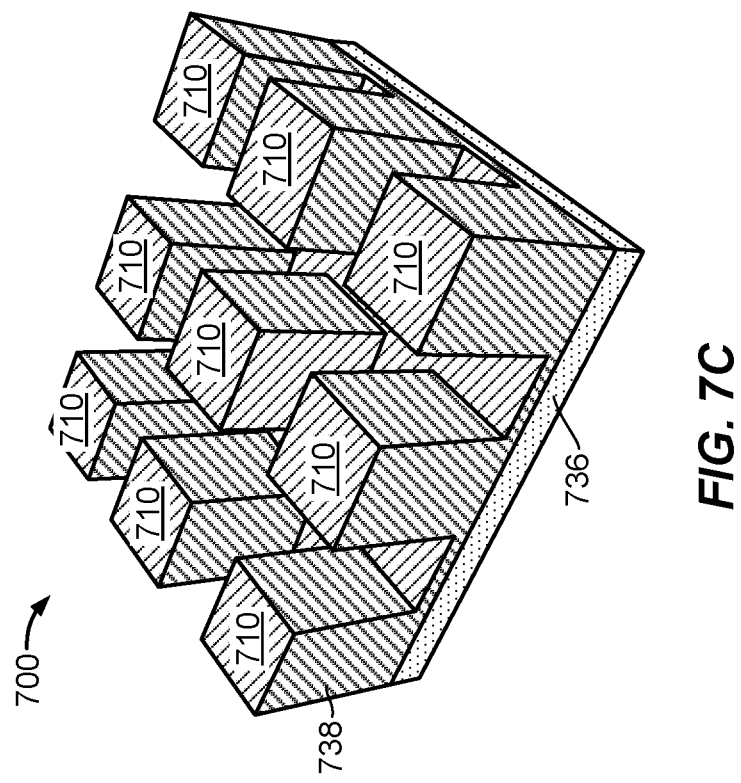
FIG. 7C generally illustrates the electrode of FIG. 7A from a tilted view.
Figure 7A:
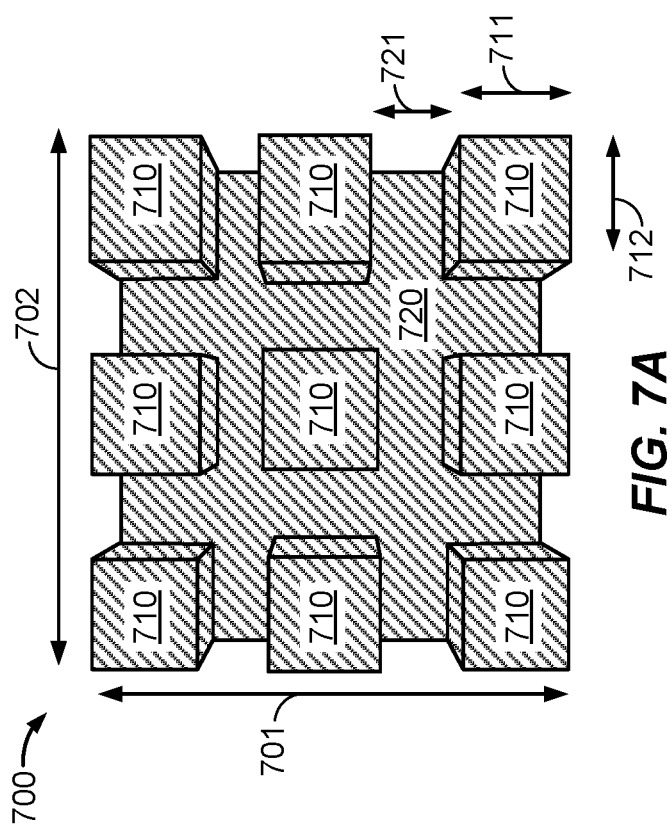
FIG. 7A generally illustrates another electrode in accordance with an aspect of the disclosure from a topographic view.
Figure 7B:
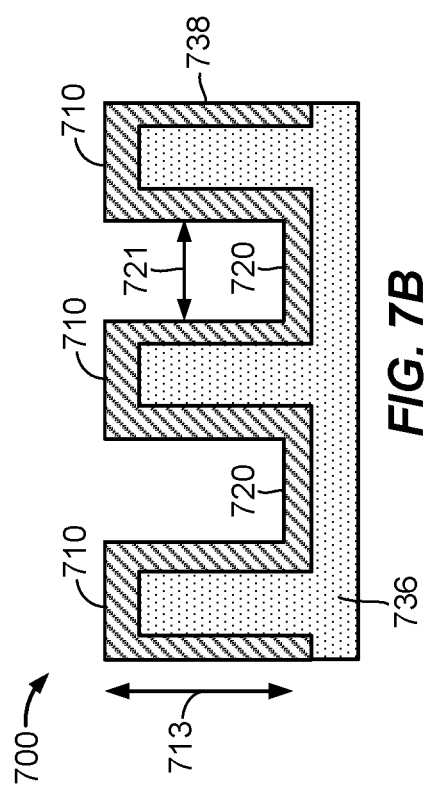
FIG. 7B generally illustrates the electrode of FIG. 7A from a cross-sectional view.

FIGS. 7A-7C generally illustrate another electrode 700 fabricated in accordance with the method of 400. FIG. 7A generally illustrates the electrode 700 from a topographic view. FIG. 7B generally illustrates the electrode 700 from a cross-sectional view. FIG. 7C generally illustrates the electrode 700 from a tilted view.

The electrode 700 includes a conductive layer 736 and a surface layer 738. The size of the footprint of the electrode 700 is defined as an electrode length 701 of the electrode 700 multiplied by an electrode width 702 of the electrode 700.

The electrode 700 further includes one or more pillars 710 and a base surface 720. Each pillar 710 may have a pillar length 711 and a pillar width 712. However, as can be seen from FIG. 7A, the pillar length 711 may be less than the electrode length 701 and the pillar width 712 may be less than the electrode width 702. A pillar 710 may be displaced from an adjacent pillar 710 by a pillar spacing distance 721.

Each pillar 710 may also have a pillar depth 713. The pillar depth 713 may be equal to a distance in a depth direction from a top surface of a pillar 710 to a top surface of the base surface 720.

As can be understood from FIGS. 7A-7C, the surface area of the surface layer 738 exceeds the size of the footprint of the electrode 700. As an example, consider a scenario wherein the electrode 700 has an electrode length 701 equal to 10 µm and an electrode width 702 equal to 10 µm. In this scenario, the footprint of the electrode 700 will be equal to one hundred square micrometers (100 µm2). If the surface layer 738 were uniform in a depth direction, then the surface area of the surface layer 738 would also be equal to 100 µm2. However, because the surface layer 738 is non-uniform in a depth direction, the surface area of the surface layer 738 will be greater than 100 µm2. For example, given a pillar length 711, pillar width 712, and pillar spacing distance 721 equal to 2 µm, and a pillar depth 713 equal to 3 µm, the surface area of the surface layer 738 will be approximately 240 µm2.

Figure 8B:
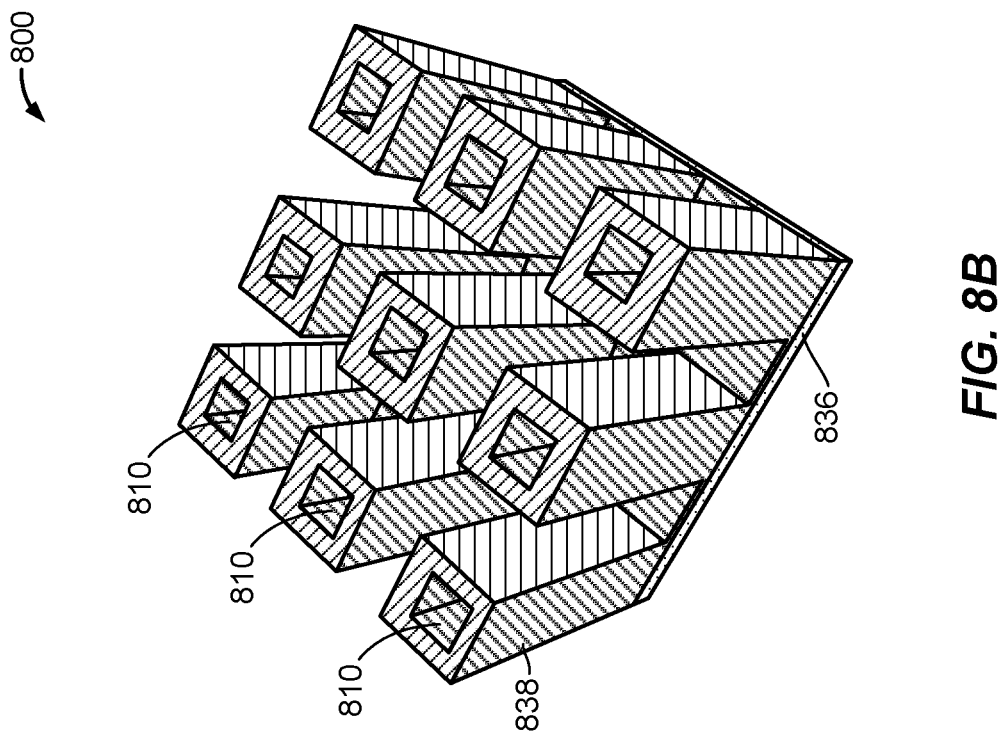
FIG. 8B generally illustrates the electrode of FIG. 8A from a tilted view.
Figure 8A:
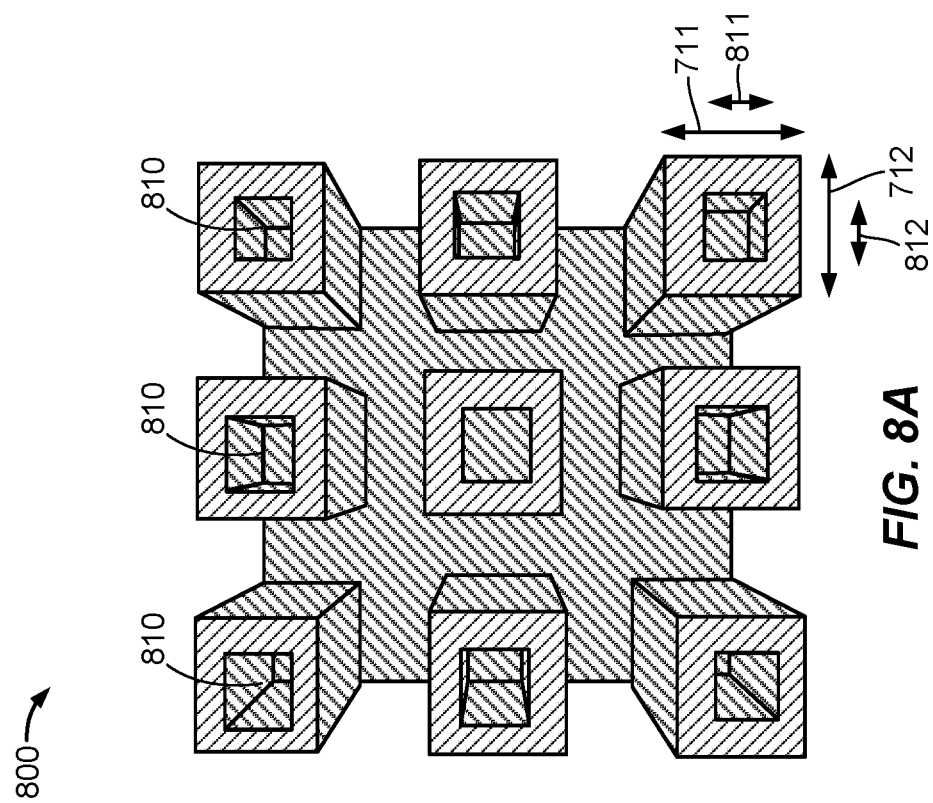
FIG. 8A generally illustrates yet another electrode in accordance with an aspect of the disclosure from a topographic view.

FIGS. 8A-8B generally illustrate yet another electrode 800 fabricated in accordance with the method of 400. FIG. 8A generally illustrates the electrode 800 from a topographic view. FIG. 8B generally illustrates the electrode 800 from a tilted view.

The electrode 800 includes a number of components that are analogous to the conductive layer 736, surface layer 738, pillars 710 and base surface 720 depicted in FIGS. 7A-7C. Accordingly, only the differences will be described here.

Unlike the pillars 710, electrode 800 includes at least one hollow pillar having a hollow 810. The hollows may have a hollow length 811 that is smaller than the pillar length 711 and a hollow width 812 that is smaller than the pillar width 712. In some implementations, the hollow depth of each hollow 810 may be equal to the pillar depth 713. As can be understood from FIGS. 8A-8B, the surface area of the surface layer 838 exceeds the size of the footprint of the electrode 800, and further exceed the surface area of the surface layer 738 of the electrode 700 depicted in FIG. 7.

While the foregoing disclosure shows various illustrative aspects, it should be noted that various changes and modifications may be made to the illustrated examples without departing from the scope defined by the appended claims. The present disclosure is not intended to be limited to the specifically illustrated examples alone. For example, unless otherwise noted, the functions, steps, and/or actions of the method claims in accordance with the aspects of the disclosure described herein need not be performed in any particular order. Furthermore, although certain aspects may be described or claimed in the singular, the plural is contemplated unless limitation to the singular is explicitly stated.

What is claimed is:

1. A deoxyribonucleic acid (DNA) sensing device formed by a process, the process comprising:
    forming a first electrode;
    forming a second electrode, wherein forming the second electrode comprises:
        forming a silver (Ag) layer;
        pressing a mold into the Ag layer to form a pattern in the Ag layer;
        removing the mold from the Ag layer; and
        exposing the Ag layer to an electrolyte;
    disposing the first electrode and the second electrode within an insulator; and
    disposing a lipid bilayer having a nanopore between the first electrode and the second electrode.

2. The DNA sensing device of claim 1, wherein the forming of the Ag layer comprises electroplating or physical vapor deposition (PVD).

3. The DNA sensing device of claim 1, wherein the forming of the Ag layer comprises forming the Ag layer on a diffusion layer and an adhesion layer comprising:
    gold (Au) and chromium (Cr);
    titanium nitride (TiN); or
    any combination thereof.

4. The DNA sensing device of claim 1, further comprising:
    heating the Ag layer to a temperature of between one-hundred-fifty and four-hundred degrees Celsius prior to the pressing of the mold; and
    cooling the Ag layer after the pressing of the mold.

5. The DNA sensing device of claim 1, wherein the mold is a polymer mold configured to form the pattern in the Ag layer.

6. The DNA sensing device of claim 1, wherein:
    the forming of the Ag layer comprises forming an Ag layer with at least one planar surface; and the forming of the pattern in the Ag layer comprises deformation of the at least one planar surface into at least one non-planar surface, wherein a surface area of the at least one non-planar surface is greater than a surface area of the at least one planar surface.

7. The DNA sensing device of claim 6, wherein the pattern is a trench.

8. The DNA sensing device of claim 6, wherein the pattern is a pillar.

9. The DNA sensing device of claim 6, wherein the pattern is a hollow pillar.

10. The DNA sensing device of claim 1, wherein the electrolyte is a chlorine electrolyte ($Cl^-$), and the exposing forms a silver chloride (AgCl) layer.

11. An electrode formed by a process, the process comprising:
   forming a substantially planar silver (Ag) layer, the layer having a surface area;
   increasing the amount of the surface area of the Ag layer by pressing a mold into the Ag layer to form a pattern in the Ag layer;
   removing the mold from the Ag layer; and
   exposing the surface area of the Ag layer to an electrolyte.

12. The electrode of claim 11, wherein the forming of the Ag layer comprises electroplating or physical vapor deposition (PVD).

13. The electrode of claim 11, wherein the forming of the Ag layer comprises forming the Ag layer on a diffusion layer and an adhesion layer comprising:
   gold (Au) and chromium (Cr);
   titanium nitride (TiN); or
   any combination thereof.

14. The electrode of claim 11, further comprising:
   heating the Ag layer to a temperature of between one-hundred-fifty and four-hundred degrees Celsius prior to the pressing of the mold; and
   cooling the Ag layer after the pressing of the mold.

15. The electrode of claim 11, wherein the mold is a polymer mold configured to form the pattern in the Ag layer.

16. The electrode of claim 11, wherein:
   the forming of the Ag layer comprises forming an Ag layer with at least one planar surface; and
   the forming of the pattern in the Ag layer comprises deformation of the at least one planar surface into at least one non-planar surface, wherein a surface area of the at least one non-planar surface is greater than a surface area of the at least one planar surface.

17. The electrode of claim 16, wherein the pattern is a trench.

18. The electrode of claim 16, wherein the pattern is a pillar.

19. The electrode of claim 16, wherein the pattern is a hollow pillar.

20. The electrode of claim 11, wherein the electrolyte is a chlorine electrolyte ($Cl^-$), and the exposing forms a silver chloride (AgCl) layer on the surface area of the Ag layer.

* * * * *